United States Patent [19]

Wakimasu et al.

[11] Patent Number: 5,330,978
[45] Date of Patent: Jul. 19, 1994

[54] PHOSPHONIC ACID DERIVATIVES AND USE THEREOF

[75] Inventors: Mitsuhiro Wakimasu; Masaaki Mori; Akira Kawada, all of Ibaraki, Japan

[73] Assignee: Takeda Chemical Industries, Ltd., Osaka, Japan

[21] Appl. No.: 892,768

[22] Filed: Jun. 3, 1992

[30] Foreign Application Priority Data

Jun. 13, 1991 [JP] Japan ................................. 3-142099
Apr. 9, 1992 [JP] Japan ................................. 4-089111

[51] Int. Cl.$^5$ ..................... C07F 9/22; A61K 33/42
[52] U.S. Cl. ................................... 514/80; 514/118; 548/414; 558/171
[58] Field of Search ............... 548/414; 514/80, 118; 558/171

[56] References Cited

U.S. PATENT DOCUMENTS

| 4,379,146 | 4/1983 | Greenlee et al. | 424/177 |
| 4,432,972 | 2/1984 | Karanewsky et al. | 424/177 |

OTHER PUBLICATIONS

Proc. Natl. Acad. Sci. USA—"Phosphorus-containing Inhibitors of Antiotensin-converting Enzyme", vol. 79, pp. 2176-2180, Apr. 1982.

Biochemistry, "Phosphonamidates as Transition-State Analogue Inhibitors of Thermolysin"—22, 4618–4624 (1982).

Biochemical and Biophysical Res. Comm., "Inhibition of Biological Actions Of Big Endothelin-1 by Phosphoramidon", vol. 172, No. 2, pp. 390-395 (1990).

Grobelny, et al., "Binding Energetics of phosphorus-containing inhibitors of Thermolysin", Biochemistry, vol. 28, No. 12, 1989, pp. 4948–4951.

Morgan et al., "Differential binding energy: A detailed evaluation of the influence of hydrogen-bonding and hydrophobic groups on the inhibition of thermolysin by phosphorus-containing inhibitors", Journal of The American Chemical Society, vol. 113, No. 1, 1991, pp. 297–307.

Kam et al., "Inhibition of thermolysin and carboxypeptidase A by phosphoramidates", Biochemstry, vol. 18, No. 14, 1979, pp. 3032–3038.

Primary Examiner—David B. Springer
Attorney, Agent, or Firm—David G. Conlin; George W. Neuner

[57] ABSTRACT

A phosphonic acid derivative compound represented by formula [I] or a pharmaceutically acceptable salt thereof:

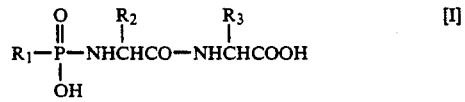

wherein $R_1$, $R_2$ and $R_3$ each represent hydrocarbon groups which may be substituted, except cases in which (1) $R_2$ is unsubstituted methyl, (2) $R_3$ is an unsubstituted hydrocarbon group having 1 to 3 carbon atoms, and (3) $R_1$ is benzyloxycarbonylaminomethyl, $R_2$ is isobutyl and $R_3$ is isobutyl or phenylmethyl, which has endothelin-converting enzyme inhibiting activity and is useful as pharmaceutical drugs such as therapeutic agents for hypertension, cardiac or cerebral circulatory diseases and renal diseases.

16 Claims, No Drawings

PHOSPHONIC ACID DERIVATIVES AND USE THEREOF

BACKGROUND OF THE INVENTION

The present invention relates to novel phosphonic acid derivatives having endothelin-converting enzyme inhibiting activity, and is further directed to methods for producing the same and their use.

Endothelin is a vasoconstrictive peptide composed of 21 amino acid residues which was isolated from the culture supernatant of the endothelin cells of porcine aortas and whose structure was determined by Yanagisawa et al. [Yanagisawa et al., Nature, 332, 411-415 (1988)]. From the research on genes coding for endothelin, as the biosynthetic mechanism of endothelin, endothelin was deduced to be biosynthesized from an endothelin precursor through big endothelin (ibid.). The subsequent studies have revealed the presence of enzymes for converting big endothelin to endothelin (endothelin-converting enzymes) [Ikekawa et al., Biochem. Biophys. Res. Commu., 171, 669-675 (1990); and Okada et al., ibid., 171, 1192-1198 (1990)].

Endothelin has vasopressor activity, so that it is anticipated to be an intrinsic factor responsible for the control of circulatory systems and deduced to be related to hypertension, cardiac or cerebral circulatory diseases and renal diseases. Inhibitors for the endothelin-converting enzymes are potential therapeutic drugs for these diseases. At present, however, no endothelin-converting enzyme inhibiting substances other than phosphoramidon are reported.

SUMMARY OF THE INVENTION

As a result of intensive investigation, the present inventors created novel compounds of the present invention having endothelin-converting enzyme inhibiting activity.

According to the present invention, there is provided a phosphonic acid derivative compound represented by formula [I] or a pharmaceutically acceptable salt thereof:

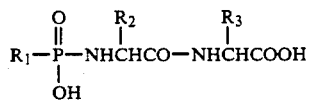

[I]

wherein $R_1$, $R_2$ and $R_3$ each represent hydrocarbon groups which may be substituted, except cases in which (1) $R_2$ is unsubstituted methyl, (2) $R_3$ is an unsubstituted hydrocarbon group having 1 to 3 carbon atoms, and (3) $R_1$ is benzyloxycarbonylaminomethyl, $R_2$ is isobutyl and $R_3$ is isobutyl or phenylmethyl. The present invention further provides a method for producing the same and use thereof.

DESCRIPTION OF THE PREFERRED EMBODIMENTS

When amino acids and peptides are indicated by abbreviations in this specification, they are based on the abbreviations adopted by the IUPAC-IUB Commission on Biochemical Nomenclature or commonly used in the art. Examples thereof are as follows:
Val: Valine
Nva: Norvaline
Leu: Leucine
Ile: Isoleucine
Nle: Norleucine
Met: Methionine
Cha: Cyclohexylalanine
Phe: Phenylalanine
Trp: Tryptophan Protective groups and reagents frequently used in this specification are indicated by the following abbreviations:
Boc: t-Butoxycarbonyl
Bzl: Benzyl
HONB: N-hydroxy-5-norbornene-2,3-dicarboximide
DCC: N,N'-dicyclohexylcarbodiimide
DCHA: N,N'-dicyclohexylamine In the compound of the present invention represented by formula [I], $R_1$, $R_2$ and $R_3$ each represent hydrocarbon groups which may be substituted, except cases in which (1) $R_2$ is unsubstituted methyl, (2) $R_3$ is an unsubstituted hydrocarbon group having 1 to 3 carbon atoms, and (3) $R_1$ is benzyloxycarbonylaminomethyl, $R_2$ is isobutyl and $R_3$ is isobutyl or phenylmethyl.

As the above-mentioned hydrocarbon group represented by $R_1$, an alkyl group, a cycloalkyl group or an aralkyl group is preferred. As the alkyl group, a straight chain or branched chain alkyl group having 1 to 12 carbon atoms is preferred. Examples thereof include methyl, ethyl, n-propyl, isopropyl, n-butyl, isobutyl, sec-butyl, tert-butyl, n-pentyl, isoamyl, tert-amyl, n-hexyl, n-octyl, n-decyl and n-dodecyl. These alkyl groups may be substituted. The substituent groups include cycloalkyl such as cyclopropyl, cyclopentyl, cyclohexyl and cycloheptyl; halogen such as fluoro, chloro and bromo; hydroxy which may be protected; alkoxy such as methoxy and ethoxy; ketone, amino which may be protected; and substituted amino. The substituted alkyl groups include, for example, cyclohexylmethyl, 2-cyclohexylethyl, 2-fluoroethyl, 2-chloroethyl, 3-chloropropyl, 2-hydroxyethyl, 2-methoxyethyl and 2-aminoethyl. As the cycloalkyl group, a 5-, 6- or 7-membered alicyclic alkyl group is preferred. Examples thereof include cyclopentyl, cyclohexyl and cycloheptyl. These cycloalkyl groups may be substituted. The substituent groups include lower alkyl such as methyl, ethyl and n-propyl; halogen such as fluoro, chloro and bromo; hydroxy which may be protected; alkoxy such as methoxy and ethoxy; ketone, amino which may be protected; and substituted amino which may be protected. The substituted cycloalkyl groups include, for example, 4-methylcyclohexyl, 4-chlorocyclo-hexyl, 4-hydroxycyclohexyl and 4-methoxycyclohexyl. As the aralkyl group, an alkyl group having 1 to 5 carbon atoms substituted by an aromatic hydrocarbon group having 6 to 12 carbon atoms is preferred. Examples thereof include phenylmethyl (benzyl), 2-phenylethyl (phenethyl), 1-naphthylmethyl, 2-naphthylmethyl, 2-(1-naphthyl)ethyl, 2-(2-naphthyl)ethyl and 3-phenylpropyl. These aralkyl groups may be substituted. The substituent groups include lower alkyl such as methyl, ethyl and n-propyl; cycloalkyl such as cyclopentyl and cyclohexyl; halogen such as fluoro, chloro and bromo; hydroxy which may be protected; and alkoxy such as methoxy and ethoxy. The substituted aralkyl groups include, for example, 4-methylphenylmethyl, 2-(4-methylphenyl)ethyl, 4-fluorophenylmethyl, 2-(4-chlorophenyl)ethyl and 2-(4-methoxyphenyl)ethyl. Preferred examples of $R_1$ include isoamyl, cyclohexylmethyl, 2-phenylethyl, 1-naphthylmethyl, 2-naphthylmethyl, 2-(1-naphthyl)ethyl and 2-(2-naphthyl)ethyl.

As the above-mentioned hydrocarbon group represented by $R_2$, an alkyl group, a cycloalkyl group or an aralkyl group is preferred. As the alkyl group, a straight chain or branched chain alkyl group having 1 to 8 carbon atoms is preferred. Examples thereof include methyl (except unsubstituted methyl), ethyl, n-propyl, isopropyl, n-butyl, isobutyl, sec-butyl, tert-butyl, n-pentyl, isoamyl, tert-amyl, n-hexyl and n-octyl. These lower alkyl groups may be substituted. The substituent groups include cycloalkyl such as cyclopentyl, cyclohexyl and cycloheptyl; halogen such as fluoro, chloro and bromo; hydroxy which may be protected; mercapto which may be protected; alkoxy such as methoxy and ethoxy; alkylthio such as methylthio and ethylthio; amino which may be protected; substituted amino which may be protected; guanidino which may be protected; carboxyl which may be protected; carbamoyl; ketone; and heterocyclic groups, wherein heterocyclic groups mean groups obtained by eliminating hydrogen atoms bound to carbon atoms of monocyclic to tricyclic heterocycles containing 1 to 3 nitrogen atoms and/or oxygen atoms and/or sulfur atoms as ring constituent atoms other than carbon atoms, for example, 2-pyridyl, 3-pyridyl, 4-pyridyl, 2-pyridazinyl, 3-furyl, 3-thienyl, 2-indolyl, 3-indolyl, 4-thiazolyl, 4-imidazolyl, benzofuryl and benzothienyl. The substituted lower alkyl groups include, for example, cyclohexylmethyl, 2-cyclo-hexylethyl, 2-fluoroethyl, 2-chloroethyl, 3-chloropropyl, hydroxymethyl, 2-hydroxyethyl, 2-methoxyethyl, 2-amino-ethyl, 4-aminobutyl, 3-guanidinopropyl, carbamoylmethyl, 2-carbamoylethyl, mercaptomethyl, carboxymethyl, 2-carboxyethyl, 4-imidazolylmethyl and 3-indolylmethyl. As the cycloalkyl group, a 5-, 6- or 7-membered alicyclic alkyl group is preferred. Examples thereof include cyclopentyl, cyclohexyl and cycloheptyl. These cycloalkyl groups may be substituted. The substituent groups include lower alkyl such as methyl, ethyl and n-propyl; halogen such as fluoro, chloro and bromo; hydroxy which may be protected; and alkoxy such as methoxy and ethoxy. The substituted cycloalkyl groups include, for example, 4-methylcyclohexyl, 4-chlorocyclohexyl, 4-hydroxycyclohexyl and 4-methoxycyclohexyl. As the aralkyl group, an alkyl group having 1 to 5 carbon atoms substituted by an aromatic hydrocarbon group having 6 to 12 carbon atoms is preferred. Examples thereof include phenylmethyl, 1-naphthylmethyl, 2-phenylethyl, 2-naphthylmethyl, 2-(1-naphthyl)ethyl, 2-(2-naphthyl)ethyl and 3-phenylpropyl. These aralkyl groups may be substituted. The substituent groups include lower alkyl such as methyl, ethyl and n-propyl; cycloalkyl such as cyclopentyl, cyclohexyl and cycloheptyl; halogen such as fluoro, chloro and bromo; hydroxy which may be protected; and alkoxy such as methoxy and ethoxy. The substituted aralkyl groups include, for example, 4-methylphenylmethyl, 2-(4-methylphenyl)ethyl, 4-fluorophenylmethyl, 2-(4-chlorophenyl)ethyl and 2-(4-methoxyphenyl)ethyl. Preferred examples of $R_2$ include n-propyl, isopropyl, isobutyl, sec-butyl, cyclohexylmethyl and benzyl, and isobutyl is particularly preferred among others.

As the above-mentioned hydrocarbon group represented by $R_3$, an alkyl group, a cycloalkyl group or an aralkyl group is preferred. As the alkyl group, a straight chain or branched chain unsubstituted alkyl group having 4 to 8 carbon atoms or a substituted alkyl group having 1 to 8 carbon atoms is preferred. Examples of the unsubstituted alkyl groups having 4 to 8 carbon atoms include n-butyl, isobutyl, sec-butyl, tert-butyl, n-pentyl, isoamyl, tert-amyl, n-hexyl, isohexyl, n-heptyl and n-octyl. The substituent groups of the alkyl groups having 1 to 8 carbon atoms such as methyl, ethyl, n-propyl, isopropyl, n-butyl, isobutyl, sec-butyl, tert-butyl, n-pentyl, isoamyl, tert-amyl, n-hexyl, isohexyl, n-heptyl and n-octyl, include cycloalkyl such as cyclopentyl, cyclohexyl and cycloheptyl; halogen such as fluoro, chloro and bromo; hydroxy which may be protected; mercapto which may be protected; alkoxy such as methoxy and ethoxy, alkylthio such as methylthio and ethylthio; amino which may be protected; substituted amino which may be protected; guanidino which may be protected; carboxyl which may be protected; carbamoyl; ketone; and heterocyclic groups, wherein heterocyclic groups mean groups obtained by eliminating hydrogen atoms bound to carbon atoms of monocyclic to tricyclic heterocycles containing 1 to 3 nitrogen atoms and/or oxygen atoms and/or sulfur atoms as ring constituent atoms other than carbon atoms, for example, 2-pyridyl, 3-pyridyl, 4-pyridyl, 2-pyridazinyl, 3-furyl, 3-thienyl, 2-indolyl, 3-indolyl, 4-thiazolyl, 4-imidazolyl, benzofuryl and benzothienyl. The substituted alkyl groups include, for example, cyclohexylmethyl, 2-cyclohexylethyl, 2-fluoro-ethyl, 2-chloroethyl, 3-chloropropyl, hydroxymethyl, 2-hydroxyethyl, 2-methoxyethyl, 2-aminoethyl, 4-aminobutyl, 3-guanidinopropyl, carbamoylmethyl, 2-carbamoylethyl, mercaptomethyl, carboxymethyl, 2-carboxyethyl, 4-imidazolylmethyl and 3-indolylmethyl. As the cycloalkyl group, a 5-, 6- or 7-membered alicyclic alkyl group is preferred. Examples thereof include cyclopentyl, cyclohexyl and cycloheptyl. These cycloalkyl groups may be substituted. The substituent groups include lower alkyl such as methyl, ethyl and n-propyl; halogen such as fluoro, chloro and bromo; hydroxy which may be protected; and alkoxy such as methoxy and ethoxy. The substituted cycloalkyl groups include, for example, 4-methylcyclohexyl, 4-chlorocyclohexyl and 4-hydroxycyclohexyl. As the aralkyl group, an alkyl group having 1 to 5 carbon atoms substituted by an aromatic hydrocarbon group having 6 to 12 carbon atoms is preferred. Examples thereof include phenylmethyl, 2-phenylethyl, 2-naphthylmethyl, 2-(1-naphthyl)ethyl, 2-(2-naphthyl)ethyl and 3-phenylpropyl. These aralkyl groups may be substituted. The substituent groups include lower alkyl such as methyl, ethyl and n-propyl; cycloalkyl such as cyclopropyl, cyclopentyl, cyclohexyl and cycloheptyl; halogen such as fluoro, chloro and bromo; hydroxy which may be protected; and alkoxy such as methoxy and ethoxy. The substituted aralkyl groups include, for example, 4-methylphenylmethyl, 2-(4-methylphenyl)ethyl, 4-fluorophenylmethyl, 2-(4-chlorophenyl)ethyl and 2-(4-methoxyphenyl)ethyl. Preferred examples of $R_3$ include 3-indolylmethyl which may be substituted.

The carbon atoms of the compound of the present invention represented by formula [I] to which $R_2$ and $R_3$ are bound are all asymmetric carbon atoms. In the present invention, these carbon atoms include all the L-, the D- and the racemic forms.

The compounds of the present invention include a compound having formula [IV] or a pharmaceutically acceptable salt thereof:

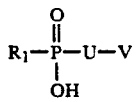 [IV]

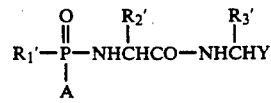 [I']

where $R_1$ is as defined previously for Compound [I] and U and V are amino acid residues connected to the P-atom at the N-terminus and selected independently from substituted or unsubstituted amino acid residues with the proviso that (1) U is not a residue of Ala, (2) V is not a residue of Ala or Val and (3) when $R_1$ is benzyloxycarbonylaminomethyl and U is a residue of Ile, V is not a residue of Ile or Phe. Preferred amino acid residues for compounds of the invention are derived from the twenty common amino acids found in proteins. Substituted amino acid residues in accord with the present invention contain substitutions as defined hereinabove with respect to $R_1$, $R_2$ and $R_3$. Such substituent hydrocarbon groups may also be used as substitutions for amino acid residues of formula IV.

The compounds of the present invention include salts of the compound represented by formula [I]. Such salts preferably include an ammonium salt, alkali metal salts such as a sodium salt and a potassium salt; alkaline earth metal salts such as a calcium salt and a magnesium salt; and organic base salts such as a pyridine salt and a triethylamine salt. Most preferably, the salts are pharmaceutically acceptable salts or salts that can be converted to pharmaceutically acceptable salts.

The compound of the present invention represented by formula [I], hereinafter occasionally referred to as compound [I] can be produced, for example, in the following manner. Namely, an organic phosphorus compound represented by formula [II], hereinafter occasionally referred to as compound [II] is reacted with a dipeptide compound represented by formula [III], hereinafter occasionally referred to as compound [III], or a salt thereof to prepare a phosphonic acid compound:

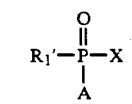 [II]

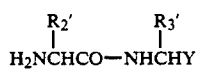 [III]

wherein A represents a protected hydroxyl group; X represents a halogen atom; Y represents a protected carboxyl group; and $R_1'$, $R_2'$ and $R_3'$ each represent hydrocarbon groups which may be substituted (for example, the groups listed hereinabove for $R_1$, $R_2$ and $R_3$, respectivley), the hydrocarbon groups being protected with protecting groups if they have groups required to be protected, except cases in which (1) $R_2'$ is unsubstituted methyl, (2) $R_3'$ is an unsubstituted hydrocarbon group having 1 to 3 carbon atoms, and (3) $R_1'$ is benzyloxycarbonylaminomethyl, $R_2'$ is isobutyl and $R_3'$ is isobutyl or phenylmethyl.

The resulting phosphonic acid compound is represented by formula [I'] and hereinafter occasionally referred to as compound [I']:

wherein A, Y, $R_1'$, $R_2'$ and $R_3'$ have the meanings given above.

This compound is subjected to treatment for eliminating the protecting groups to obtain compound [I]. In some cases, the protecting groups are eliminated concurrently with the reaction of phosphorus compound [II] with dipeptide compound [III] or the salt thereof, whereby compound [I] can be obtained without treatment for eliminating the protecting groups.

"A" of organic phosphorus compound [II] is the protected hydroxyl group. As the protecting group, a known protecting group for P-OH is used. Specifically preferred such protecting groups include benzyl and 4-methylbenzyl. "X" of organic phosphorus compound [II] is halogen, for example, chloro, bromo or iodo. "Y" of dipeptide compound [III] is the protected carboxyl group. As the protecting group, a known protecting group for a carboxyl group is used. Specifically preferred such protecting groups include benzyl and 4-methylbenzyl. The salt of dipeptide compound [III] preferably means a salt at the terminal amino group. Such salts include salts with inorganic acids such as hydrochloric acid and sulfuric acid; and salts with organic acids such as acetic acid and p-toluenesulfonic acid.

Described in more detail, this method comprises reacting organic phosphorus compound [II] with dipeptide compound [III] in an organic solvent, followed by treatment for eliminating the protecting groups to obtain the, desired compound-[I]. It is generally preferred to isolate the first reaction product, i.e. resulting phosphonic acid compound [I'], before removing the protecting groups.

The organic solvent is selected from organic solvents which do not react with compounds [II] and [III]. Organic solvents preferably used are ether solvents such as tetrahydrofuran and dioxane, and halogenated hydrocarbon solvents such as dichloromethane and dichloroethane. Dichloromethane is most suitable among others. These solvents are preferably used in the anhydrous state. The amount of the organic solvent is usually about 10 to 100 ml/mmol of compound [III] and more preferably about 30 to 50 ml/mmol. Compound [II] is usually used in the same amount as that of compound [III] or in excess, specifically in an amount of 1 to 2.5 mmol/mmol of compound [III] and preferably in an amount of 1 to 1.5 mmol/mmol. The reaction of compound [II] with compound [III] is dehydrohalogenation reaction.

Bases are preferably used to eliminate hydrogen halides. Such bases used include inorganic bases such as sodium hydroxide and potassium hydroxide; and organic bases such as triethylamine and N-methylmorpholine; and the organic bases are more preferable among others. The bases are used in an amount enough to neutralize the hydrogen halides and the salts of compound [III], or in an amount of more than that. In some cases, liquid organic bases such as pyridine are used partly for solvents.

The reaction is conducted under cooling or at room temperature, usually at a temperature of about 0° to 25°

C. The reaction time is usually 0.5 to 2 hours, though it varies depending on the kind of starting compound and the reaction temperature. After reaction, compound [I'] can be isolated from the reaction solutions by combinations of known purifying techniques such as solvent extraction, distillation, column chromatography, liquid chromatography and recrystallization.

Protecting group eliminating reagents may be further added to the reaction Solutions containing compound [I'] to produce the desired compound [I]. The protecting groups of compound [I'] can be eliminated using known protecting group eliminating reagents, according to known methods, although they may vary depending on the kind of protecting groups as is well known to those skilled in the art. After treatment for elimination of the protecting groups, compound [I] can be isolated from the reaction solutions by combinations of known purifying techniques such as solvent extraction, distillation, column chromatography, liquid chromatography and recrystallization. As a matter of course, treatment for isolation of compound [I'] prior to eliminating the protecting groups typically makes purification of the desired compound [I] easier than without isolation of compound [I'].

Compounds [II] and [III] used as starting compounds are commercially available or can be produced by or in accordance with methods known in the art.

Compound [I] of the present invention, including the pharmaceutically acceptable salts thereof, are useful as pharmaceutical drugs such as therapeutic agents for hypertension, cardiac or cerebral circulatory diseases and renal diseases. The pharmaceutically acceptable salts include, for example, an ammonium salt; alkali metal salts such as a sodium salt and a potassium salt; alkaline earth metal salts such as a calcium salt and a magnesium salt; and organic base salts such as a pyridine salt and a triethylamine salt. As these therapeutic agents, compound [I] can be administered in a treatment effective amount orally or parenterally in the form of a liquid formulation or a solid formulation to mammals such as humans, rabbits, dogs, cats, rats and mice. Usually, it is administered parenterally in the form of a liquid formulation, such as an injection. The dosage varies depending on the type of disease to be treated, the symptoms of the disease, the object to which the drug is given and the route of administration. For example, when parenterally given to human adult for treatment of hypertension, it is advantageous that compound [I] is given in the form of an injection by intravenous injection in one dose of about 0.01 to 20 mg/kg of weight, preferably about 0.05 to 10 mg/kg about once to 3 times a day. In the case of other routes and forms of administration, compound [I] can also be given in a dose similar thereto. The injections include subcutaneous injections, intracutaneous injections, intramuscular injections and drip injections, as well as intravenous injections. Such injections are prepared by methods known per se in the art, namely by dissolving, suspending and emulsifying compound [I] in sterile aqueous solutions or oily solutions. The aqueous solutions for injection include physiological saline and isotonic solutions containing glucose or other adjuvants, and may be used in combination with appropriate solubilizers such as alcohols, e.g. ethanol; polyalcohols, e.g. propylene glycol and polyethylene glycol; and nonionic surface active agents, e.g. Polysolvate 80 and HCO-50. The oily solutions include sesame oil and soybean oil, and may be used in combination with solubilizers such as benzyl benzoate and benzyl alcohol. The injections thus prepared are usually packed in appropriate capsules. Conveniently, compound [I] is packaged in a unit dose in a pharmaceutically acceptable carrier in a capsule or tablet form, or in a vial. The unit does contains an amount of compound [I], as set forth above, for one administration to a patient. Typically, the unit dose will contain from about 0.5 to about 1500 mg, preferably about 2.5 to about 750 mg, of compound [I]. Vials can also conveniently be packaged for multiple doses for treatment for a prescribed period of time.

Compound [I] of the present invention has endothelin-converting enzyme inhibiting activity as shown by the procedures described in the Test Example. Endothelin is a peptide having vasoconstrictive activity, and therefore compound [I] is useful as pharmaceutical drugs such as therapeutic agents for hypertension, cardiac or cerebral circulatory diseases and renal diseases.

The present invention will be described in more detail with the following test example, reference example and examples. It is understood of course that these test example, reference example and examples are not intended to limit the scope of the invention. In the examples, all amino acids other than glycine take the L-form unless otherwise specified. In the examples, silica gel 60F-254 (Merck) was used as plates of thin layer chromatography, and $Rf^1$: chloroform-methanol (9:1) and $Rf^2$: isopropanol-water-concentrated aqueous ammonia (5:2:0.2) were used as developing solvents.

TEST EXAMPLE

Measurement of Endothelin-Converting Enzyme Inhibiting Activity of Phosphonic Acid Amide Derivatives In 1.5-ml centrifugal tube (BIO-BIK), 80 μl of 50 mM bis-Trispropane-hydrochloric acid buffer (pH 7.2) supplemented with 1.0 mg/ml bovine serum albumin, 0.1M sodium chloride, 1.0 mM phenylmethanesulfonyl fluoride (PMSF, Wako Pure Chemical Industries), 1.0 μg/ml leupeptin (Peptide Institute Inc.), 1.0 μg/ml chymostatin (Peptide Institute Inc.), 1.0 μg/ml pepstatin A (Peptide Institute Inc.), 1.0 μM E-64 (Peptide Institute Inc.), 1.0 μm thiorphan (Sigma) and 1.0 μM angiotensin-converting enzyme inhibitor [CV-5975, Inada et al., *Japanese Journal of Pharmacology*, 47, 135-141 (1988)], 5 μl of a sample solution to be tested (an aqueous solution or an aqueous solution containing 2% dimethyl sulfoxide) or 5 μl of distilled water for the control plot, and 10 μl of an endothelin-converting enzyme sample prepared as described in the following reference example were placed. After standing at 37° C. for 30 minutes, 5 μl of a substrate solution [physiological phosphate buffer (PBS, containing 0.2 g of potassium chloride, 0.2 g of potassium dihydrogenphosphate, 8.0 g of sodium chloride and 1.14 g of disodium hydrogenphosphate in 1,000 ml of distilled water) supplemented with $1.0 \times 10^{-6}$M pig big endothelin I (1-39) (Peptide Institute Inc.) and 1.0 mg/ml bovine serum albumin] was added thereto to initiate enzyme reaction. After reaction at 37° C. for 1 hour, the reaction mixture was boiled in boiling water for 5 minutes, thereby terminating the reaction. The resulting insoluble material was removed by centrifugation, and endothelin I (1-21) produced by the enzyme reaction contained in 10 μl of the supernatant was quantified by the endothelin I-specific sandwich enzyme immunoassay method already established [Suzuki et al., *J. Immunol. Meth.*, 188, 245-250 (1989)], and compared with the amount of endothelin produced in the control plot to evaluate the enzyme inhibiting activity. The endothelin-converting enzyme inhibiting activity of the phosphonic acid derivatives of the present invention is shown in the following table. The inhibiting activity is indicated by the concentration of inhibitors required to provide 50% inhibition based on the amount converted to endothelin I in the control plot, namely the 50% inhibition concentration (IC50).

Inhibiting Activity of Phosphonic Acid Derivatives of the Present Invention on Endothelin-Converting Enzyme

| Compound | IC50 ($\mu$M) |
| --- | --- |
| N-(Phenethylphosphonyl)-Leu—Trp.2Na | 0.2 |
| N-(Isoamylphosphonyl)-Leu—Trp.2Na | 0.7 |
| N-(Cyclohexylmethylphosphonyl)-Leu—Trp.2Na | 0.4 |
| N-(Phenethylphosphonyl)-Phe—Trp.2Na | 0.5 |
| N-(Phenethylphosphonyl)-Ile—Trp.2Na | 1.2 |
| N-(Phenethylphosphonyl)-Val—Trp.2Na | 2.8 |
| N-(Phenethylphosphonyl)-Cha—Trp.2Na | 1.0 |
| N-(Phenethylphosphonyl)-Nle—Trp.2Na | 1.4 |
| N-(Phenethylphosphonyl)-Leu—Phe.2Na | 5.7 |
| N-(Phenethylphosphonyl)-Leu—Leu.2Na | 4.8 |
| N-(1-Naphthylmethylphosphonyl)-Leu—Trp.2Na | 0.2 |
| N-(2-Naphthylmethylphosphonyl)-Leu—Trp.2Na | 1.0 |
| N-[2-(1-Naphthyl)ethylphosphonyl]-Leu—Trp.2Na | 0.4 |
| N-[2-(2-Naphthyl)ethylphosphonyl]-Leu—Trp.2Na | 0.1 |

REFERENCE EXAMPLE

1. Preparation of Endothelin-Converting Enzyme Sample for Assaying Enzyme Inhibiting Activity As endothelin-converting enzymes existing in organisms, two kinds of metalloenzymes different in enzymological properties are generally known. One exits in the cytoplasms, and the other is membrane-bound. The latter is characterized by that it is inhibited with phosphoramidon known as an inhibitor for metalloproteases [Matsumura et al., FEBS Lett., 272, 166–170 (1990)]. The endothelin-converting enzyme in the present invention means the membrane-bound enzyme of these two kinds of enzymes.

One example of the preparation thereof is hereinafter described.

About 500 g of the pig lung (of one pig) was sliced and disrupted in 2.0 liter of PBS supplemented with 0.05% sodium azide, 1.0 mM dithiothreitol, 1.0 mM PMSF, 1.0 $\mu$g/ml leupeptin, 1.0 $\mu$g/ml chymostatin, 1.0 $\mu$g/ml pepstatin A and 1.0 $\mu$M E-64, and then homogenized (1 minute$\times$5 times) by a Polytron mixer (KINEMATICA). The centrifuged supernatant (240$\times$G, 5 minutes) was further centrifuged at 10,000$\times$G for 15 minutes, and the resulting supernatant was subjected to ultracentrifuge (100,000$\times$G, 90 minutes) to obtain membrane fraction as a precipitate. To this precipitate, 1.0% Triton X-100 was added to solubilize enzyme activity. The protein amount of the solubilized membrane fractions was about 2.3 g. This was diluted to 2.0 mg of protein/ml to use for assaying the activity of enzyme inhibitors.

2. Measurement of Molecular Weight of Endothelin-Converting Enzyme 2.0 ml of an enzyme solution obtained by treatment similar to that described above using 1.0% 3-[(3-cholamidopropyl)dimethylammonio]-1-propanesulfonic acid (CHAPS) in place of 1.0% Triton X-100 as the solubilizing agent was subjected to gel filtration using a HiLoad 16/60 Superdex 200 pg column (Pharmacia, 1.6$\times$600 mm) pre-equilibrated with 50 mM Tri-hydrochloric acid buffer (pH 8.0) supplemented with 0.1% CHAPS, 0.15M sodium chloride, 0.02% sodium azide, 0.1 mM PMSF, 1.0 $\mu$g/ml leupeptin, 1.0 $\mu$g/ml pepstatin A and 1.0 $\mu$M E-64. The same buffer as used for equilibration was used as an elution, and the flow rate was 0.5 ml/minute. Separately taking 5.0 ml of each eluate, the endothelin-converting enzyme activity of each fraction was assayed. The molecular weight of this enzyme was estimated to be about 300,000 from a comparison between the elution position of the enzyme activity and that of the standard position for calibration of molecular weight analyzed under the same conditions. Chromatography was conducted using a BioPilot system (Pharmacia).

3. Various Properties of Endothelin-Converting Enzyme 3-1. Optimum Ph

Using bis-Tris-hydrochloric acid buffer, Tris-hydrochloric acid buffer or diethanolamine-hydrochloric acid buffer, the enzyme activity was assayed at various pHs. As a result, this enzyme has an optimum pH around pH 7.5

3-2. Behavior to Various Protease Inhibitors

The inhibiting ratio of various protease inhibitors to this enzyme is shown in the following table. This enzyme was not inhibited so much be a specific enzyme inhibitor to each of serine protease, SH protease and acid protease, and was inhibited by o-phenanthroline or ethylenediaminetetraacetic acid which is a metal chelating agent inhibiting the activity of metalloprotease, and by phosphoramidone known as a metalloprotease inhibitor. From the above, this enzyme was concluded to be a metalloenzyme. This enzyme was also inhibited by an SH reagent. A similar phenomenon is known to be observed in some kind of metalloprotease.

Inhibition Effect of Various Protease Inhibitors on Endothelin-Converting Enzyme

| Inhibitor | Concentration ($\mu$M) | Inhibiting Ratio (%) |
| --- | --- | --- |
| Serine protease inhibitor | | |
| PMSF | 1000 | 32 |
| Leupeptin | 100 | 23 |
| Chymostatin | 100 | 2 |
| SH protease inhibitor E-64 | 100 | 9 |
| SH reagent Dithiothreitol | 1000 | 96 |
| Acid protease inhibitor Pepstatin | 100 | 20 |
| Metalloprotease inhibitor | | |
| o-Phenanthroline | 1000 | 92 |
| Ethylenediaminetetra-acetic acid | 1000 | 70 |
| Phosphoramidone | 100 | 70 |

3-3. Metal Requirement

Since this enzyme is a metalloenzyme, the metal requirement was examined. Various metals was added to the enzyme in the presence of o-phenanthroline to examine the restoration of its activity. As a result, this revealed that the activity of this enzyme was not restored by addition of copper (divalence), but restored by addition of any metal ions of manganese (divalence), zinc (divalence) and cobalt (divalence). This enzyme is therefore likely to contain any of these three kinds of metals at its active center.

3-4. Influence of Temperature

The activity of this enzyme at 37° C. is more than 3 times that at 25° C.

3-5. Kinetic Coefficient

The Michaelis coefficient of this enzyme to pig big endothelin was calculated to be about $5 \times 10^{-6}$M from the Lineweaver-Burk plot.

EXAMPLE 1

N-(Phenethylphosphonyl)-Leu-Trp.2Na (1) Boc-Leu-Trp-OBzl

Trp-OBzl.HCl (purchased from Kokusan Kagaku) (8.39 g) was dissolved in N,N-dimethylformamide (200 ml), and triethylamine (3.90 ml) and Boc-Leu-ONB [prepared from Boc-Leu-OH.H$_2$O (6.32 g), HONB (4.77 g) and DCC (5.49 g)] were added thereto under ice cooling, followed by stirring for 12 hours. The solvent was removed by distillation under reduced pressure, and the residue was dissolved in ethyl acetate. The resulting solution was washed with water, 10% aqueous citric acid, water, saturated aqueous sodium hydrogencarbonate and water in this order. After drying with anhydrous sodium sulfate, the solvent was removed by distillation to obtain a crude product. Recrystallization from ethyl acetate-petroleum ether gave needle crystalline colorless Boc-Leu-Trp-OBzl (10.3 g).

Melting point: 131°–132° C., TLC Rf$^1$ 0.59

$[\alpha]^D_{25} = -23.8°$ (C=1.04, MeOH)

elemental analysis: as C$_{29}$H$_{37}$N$_3$O$_5$ Calculated: C: 68.62; H: 7.35; N: 8.28. Found: C: 68.46; H: 7.53; N: 8.30.

(2) N-(O-Benzyl-P-Phenethylphosphonyl)-Leu-Trp-OBzl 1,2-Ethanedithiol (0.2 ml) and 8N hydrochloric acid-dioxane (20 ml) were added to Boc-Leu-Trp-OBzl (1.20 g) obtained in (1) under ice cooling to dissolve it, followed by stirring for 30 minutes. The solvent was removed by distillation under reduced pressure, and diethyl ether was added to the residue to precipitate crystals. The crystals were filtered off, and dried. The resulting product was suspended in dichloromethane, and triethylamine (0.66 ml) and O-benzyl-P-phenethyl phosphochloridate [prepared from dibenzylphenethyl phosphonate (868 mg) and phosphorus pentachloride (544 mg) by the method described in E. D. Thorsett et al., *Proc. Natl. Acad. Sci. USA*, 79, 2176 (1982)] were added thereto under ice cooling, followed by stirring for 12 hours. Dichloromethane (50 ml) was added to the reaction solution for dilution, and then water was added thereto. After stirring for 10 minutes, the product was extracted with dichloromethane. The resulting dichloromethane solution was washed with 10% aqueous citric acid, water, saturated aqueous sodium hydrogencarbonate and water in this order. After drying with anhydrous sodium sulfate, the solvent was removed by distillation. The residue was purified by silica gel column chromatography. A crude product was obtained from fractions eluted with chloroform. Recrystallization from ethyl acetate-petroleum ether gave needle crystalline colorless N-(O-benzyl-P-phenethylphosphonyl)-Leu-Trp-OBzl (580 mg).

Melting point: 85°–87° C., TLC Rf$^1$ 0.31

Elemental analysis: as C$_{39}$H$_{44}$N$_3$O$_5$P Calculated: C: 70.36; H: 6.66; N: 6.31. Found: C: 70.10; H: 6.64; N: 6.23.

IR $\nu$max(KBr)cm$^{-1}$: 1740 (C=O), 1660 (NHC=O), 1560 (Ar), 1190 (P=O)

NMR $\delta$ppm(CDCl$_3$): 0.81–0.88 (6H, m), 1.27–1.37 (1H, m), 1.50–1.56 (1H, m), 1.60–1.70 (1H, m), 1.78–1.91 (1H, m), 1.93–2.00 (1H, m), 2.72–2.93 (3H, m), 3.25–3.30 (2H, m), 3.73–3.88 (1H, m), 4.71–5.10 (5H, m), 6.75–7.90 (22H, m)

(3) N-(Phenethylphosphonyl)-Leu-Trp.2Na

N-(O-Benzyl-P-phenethylphosphonyl)-Leu-Trp-OBzl (70.0 mg) obtained in (2) and sodium hydrogencarbonate (7.7 mg) were dissolved in methanol-water (10:1) (11 ml), and 10% palladium-carbon (20 mg) was added thereto to conduct catalytic reduction in a stream of hydrogen at ordinary temperature at ordinary pressure for 1.5 hours. The catalyst was removed by filtration, and the filtrate was concentrated under reduced pressure, followed by addition of water. Lyophilization gave powdery N-(phenethylphosphonyl)-Leu-Trp.2Na (40.3 mg).

TLC Rf$^2$ 0.58

LSIMS: m/z=530.2 [M+H$^+$]

EXAMPLE 2

N-(Phenethylphosphonyl)-Ile-Trp.2Na (1) Boc-Ile-Trp-OBzl

Trp-OBzl.HCl (purchased from Kokusan Kagaku) (8.39 g) was condensed with BOC-Ile-ONB [prepared from Boc-Ile-OH.0.5H$_2$O (6.09 g), HONB (4.77 g) and DCC (5.49 g)] in a manner similar to that of Example 1-(1) to obtain needle crystalline colorless Boc-Ile-Trp-OBzl (8.02 g).

Melting point: 111°–112° C., TLC Rf$^1$ 0.56

$[\alpha]^D_{25} = -25.5°$ C. (C=1.05, MeOH)

Elemental analysis: as C$_{29}$H$_{37}$N$_3$O$_5$ Calculated: C: 68.62; H: 7.35; N: 8.28. Found: C: 68.50; H: 7.57; N: 8.23.

(2) N-(O-Benzyl-P-Phenethylphosphonyl)-Ile-Trp-OBzl 1,2-Ethanedithiol (0.2 ml) and 8N hydrochloric acid-dioxane (20 ml) were added to Boc-Ile-Trp-OBzl (1.62 g) obtained in (1) under ice cooling to dissolve it, followed by stirring for 30 minutes. The solvent was removed by distillation under reduced pressure, and diethyl ether was added to the residue to precipitate crystals. The crystals were filtered off, and dried. The resulting product was reacted with O-benzyl-P-phenethyl phosphochloridate [prepared from dibenzylphenethyl phosphonate (1.17 g) and phosphorus pentachloride (800 mg)] in a manner similar to that of Example 1-(2) to obtain needle crystalline colorless N-(O-benzyl-P-phenethylphosphonyl)-Ile-Trp-OBzl (390 mg).

Melting point: 151°–152° C., TLC Rf$^1$ 0.23

Elemental analysis: as C$_{39}$H$_{44}$N$_3$O$_5$P Calculated: C: 70.36; H: 6.66; N: 6.31. Found: C: 70.10; H: 6.64; N: 6.23.

IR $\nu$max(KBr)cm$^{-1}$: 1730 (C=O), 1660 (NHC=O), 1540 (Ar), 1200 (P=O)

NMR $\delta$ppm(CDCl$_3$): 0.70–0.88 (6H, m), 0.93–1.03 (1H, m), 1.33–1.42 (1H, m), 1.63–1.76 (1H, m), 1.79–1.93 (1H, m), 1.93–2.02 (1H, m), 2.55–2.91 (2H, m), 2.94–3.02 (1H, m), 3.19–3.22 (2H, m), 3.59–3.67 (1H, m), 4.73–5.11 (5H, m), 6.51–7.87 (22H, m)

(3) N-(Phenethylphosphonyl)-Ile-Trp.2Na

N-(O-Bezel-P-phenethylphosphonyl)-Ile-Trp-OBzl (70.0 mg) obtained in (2) was subjected to catalytic reduction in a manner similar to that of Example 1-(3) to obtain powdery N-(phenethyl-phosphonyl)-Ile-Trp.2Na (45.8 mg).

TLC Rf$^2$ 0.58

LSIMS: m/z=530.2 [M+H$^+$]

EXAMPLE 3

N-(Phenethylphosphonyl)-Val-Trp.2Na (1) Boc-Val-Trp-OBzl

Trp-OBzl. HCl (purchased from Kokusan Kagaku) (500 g) was condensed with Boc-Val-ONB [prepared from Boc-Val-OH (3.28 g), HONB (2.84 g) and DCC (3.27 g)] in a manner similar to that of Example 1-(1) to obtain needle crystalline colorless Boc-Val-Trp-OBzl (4.88 g).

Melting point: 139°–140° C., TLC Rf[1] 0.44

$[\alpha]^D{}_{25} = -21.8°$ (C=1.04, MeOH)

Elemental analysis: as $C_{28}H_{35}N_3O_5$ Calculated: C: 68.13; H: 7.15; N: 8.51. Found: C: 68.13; H: 7.08; N: 8.51.

(2) N-(O-Benzyl-P-Phenethylphosphonyl)-Val-Trp-OBzl 1,2-Ethanedithiol (0.2 ml) and 8N hydrochloric acid-dioxane (20 ml) were added to Boc-Val-Trp-OBzl (1.58 g) obtained in (1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-phenethyl phosphochloridate [prepared from dibenzylphenethyl phosphonate (1.17 g) and phosphorus pentachloride (800 mg)] in a manner similar to that of Example 1-(2) to obtain needle crystalline colorless N-(O-benzyl-P-phenethylphosphonyl)-Val-Trp-OBzl (337 mg).

Melting point: 143°–144° C., TLC Rf[1] 0.23

Elemental analysis: as $C_{38}H_{42}N_3O_5P \cdot 0.25H_2O$ Calculated: C: 69.55; H: 6.52; N: 6.40 Found: C: 69.53; H: 6.78; N: 6.31

IR $\nu$max(KBr)cm$^{-1}$: 1740 (C=O), 1660 (NHC=O), 1550 (Ar), 1200 (P=O)

NMR $\delta$ppm(CDCl$_3$): 0.78–0.83 (3H, m), 0.87–0.92 (3H, m), 1.83–2.06 (3H, m), 2.76–2.93 (2H, m), 2.99–3.10 (1H, m), 3.19–3.32 (2H, m), 3.56–3.66 (1H, m), 4.22–5.60 (5H, m), 6.55–7.91 (22H, m)

(3) N-(Phenethylphosphonyl)-Val-Trp.2Na

N-(O-Benzyl-P-phenethylphosphonyl)-Val-Trp-OBzl (70.0 mg) obtained in (2) was subjected to catalytic reduction in a manner similar to that of Example 1-(3) to obtain powdery N-(phenethylphosphonyl)-Val-Trp.2Na (40.3 mg).

TLC Rf[2] 0.58

LSIMS: m/z=516.1 [M+H$^+$]

EXAMPLE 4

N-(Phenethylphosphonyl)-Phe-Trp.2Na (1) Boc-Phe-Trp-OBzl

Trp-OBzl.HCl (purchased from Kokusan Kagaku) (5.00 g) was condensed with Boc-Phe-ONB [prepared from Boc-Phe-OH (4.01 g), HONB (2.84 g) and DCC (3.27 g)] in a manner similar to that of Example 1-(1) to obtain needle crystalline colorless Boc-Phe-Trp-OBzl (7.98 g).

Melting point: 129°–130° C., TLC Rf[1] 0.48

$[\alpha]^D{}_{25} = -4.1°$ (C=1.04, MeOH)

Elemental analysis: as $C_{32}H_{35}N_3O_5$ Calculated: C: 70.96; H: 6.51; N: 7.76. Found: C: 70.70; H: 6.72; N: 7.53.

(2) N-(O-Benzyl-P-Phenethylphosphonyl)-Phe-Trp-OBzl 1,2-Ethanedithiol (0.2 ml) and 8N hydrochloric acid-dioxane (20 ml) were added to Boc-Phe-Trp-OBzl (1.73 g) obtained in (1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-phenethyl phosphochloridate [prepared from dibenzylphenethyl phosphonate (1.17 g) and phosphorus pentachloride (800 mg)] in a manner similar to that of Example 1-(2) to obtain needle crystalline colorless N-(O-benzyl-P-phenethylphosphonyl)-Phe-TrP-OBzl (452 mg).

Melting point: 54°–55° C. TLC Rf[1] 0.30

Elemental analysis: as $C_{42}H_{42}N_3O_5P$ Calculated: C: 72.09; H: 6.05; N: 6.00. Found: C: 69.71; H: 6.42; N: 5.75.

IR $\nu$max(KBr)cm$^{-1}$: 1740 (C=O), 1660 (NHC=O), 1500 (Ar), 1200 (P=O)

NMR $\delta$ppm(CDCl$_3$): 1.45–1.68 (2H, m), 2.50–2.66 (2H, m), 2.72–3.03 (3H, m), 3.12–3.30 (2H, m), 4.01–4.15 (1H, m), 4.36–4.64 (1H, m), 4.75–4.83 (1H, m), 4.41–5.09 (3H, m), 6.60–7.87 (2H, m)

(3) N-(phenethylphosphonyl)-Phe-Trp.2Na

N-(O-Benzyl-p-phenethylphosphonyl)-Phe-TrP-OBzl (70 mg) obtained in (2) was subjected to catalytic reduction in a manner similar to that of Example 1-(3) to obtain powdery N-(phenethylphosphonyl)-Phe-Trp.2Na (45.0 mg).

TLC Rf[2] 0.58

LSIMS: m/z=564.1 [M+H$^+$]

EXAMPLE 5

N-(phenethylphosphonyl)-Cha-Trp.2Na (1) Boc-Cha-Trp-OBzl

Trp-OBzl.HCl (purchased from Kokusan Kagaku) (1.65 g) was condensed with Boc-Cha-ONB [prepared from Boc-Cha-OH.DCHA (purchased from Nova Biochem) (2.26 g), HONB (941 mg) and DCC (1.08 g)] in a manner similar to that of Example 1-(1) to obtain needle crystalline colorless Boc-Cha-Trp-OBzl (2.12 g).

Melting point: 67°–68° C., TLC Rf[1] 0.70

$[\alpha]^D{}_{25} = -14.9°$ (C=1.02, MeOH)

Elemental analysis: as $C_{32}H_{41}N_3O_5$ Calculated: C: 70.18; H: 7.55; N: 7.67. Found: C: 70.23; H: 7.84; N: 7.38.

(2) N-(O-Benzyl-P-Phenethylphosphonyl)-Cha-TrP-OBzl 1,2-Ethanedithiol (0.2 ml) and 8N hydrochloric acid-dioxane (20 ml) were added to Boc-Cha-Trp-OBzl (1.75 g) obtained in (1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-phenethyl phosphochloridate [prepared from dibenzylphenethyl phosphonate (1.17 g) and phosphorus pentachloride (800 mg)] in a manner similar to that of Example 1-(2) to obtain needle crystalline colorless N-(O-benzyl-p-phenethylphosphonyl)-Cha-Trp-OBzl (41o mg).

Melting point: 107°–109° C., TLC Rf[1] 0.28

Elemental analysis: as $C_{42}H_{48}N_3O_5P$ Calculated: C: 71.47; H: 6.85; N: 5.95. Found: C: 71.38; H: 6.93; N: 5.58.

IR $\nu$max(KBr)cm$^{-1}$: 1750 (C=O), 1660 (NHC=O), 1500 (Ar), 1200 (P=O)

NMR $\delta$ppm(CDCl$_3$): 0.76–0.93 (2H, m), 1.04–1.21 (3H, m), 1.26–1.41 (2H, m), 1.53–1.73 (6H, m), 1.84–2.01 (2H, m), 2.71–2.91 (3H, m), 3.24–3.31 (2H, m), 3.78–3.87 (1H, m), 4.70–5.11 (5H, m), 6.71–7.96 (22H, m)

(3) N-(Phenethylphosphonyl)-Cha-Trp.2Na

N-(O-Benzyl-P-phenethylphosphonyl)-Cha-Trp-OBzl (70.6 mg) obtained in (2) was subjected to catalytic reduction in a manner similar to that of Example 1-(3) to obtain powdery N-(phenethylphosphonyl)-Val-Trp.2Na (38.4 mg).

TLC Rf[2] 0.58

LSIMS: m/z=570.2 [M+H$^+$]

EXAMPLE 6

N-(phenethylphosphonyl)-Nle-Trp.2Na (1) Boc-Nle-Trp-OBzl

Trp-OBzl.HCl (purchased from Kokusan Kagaku) (1.65 g) was condensed with Boc-Nle-ONB [prepared from Boc-Nle-OH.DCHA (purchased from Nova Biochem) (2.06 g), HONB (941 mg) and DCC (1.08 g)] in a manner similar to that of Example 1-(1) to obtain oily light yellow Boc-Nle-Trp-OBzl (2.41 g).

TLC $Rf^1$ 0.55

LSIMS: m/z=508.2 (M+)

IR $\nu$max(KBr)cm$^{-1}$: 1680 (NHC=O), 1510 (Ar)

NMR $\delta$ppm(CDCl$_3$): 0.83 (3H, t), 1.18-1.31 (4H, m), 1.41 (9H, s), 1.65-1.80 (2H, m), 3.25-3.35 (2H,m), 4.04 (1H, broad,s), 4.40-4.99 (2H, m), 5.07 (2H, s), 6.50-6.55 (1H, m), 6.84-7.51 (10H,m), 8.13 (1H, broad, s)

(2) N-(O-Benzyl-P-Phenethylphosphonyl)-Nle-Trp-OBzl 1,2-Ethanedithiol (0.2 ml) and 8N hydrochloric acid-dioxane (20 ml) were added to Boc-Nle-Trp-OBzl (1.62 g) obtained in (1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-phenethyl phosphochloridate prepared from dibenzylphenethyl phosphonate (1.17 g) and phosphorus pentachloride (800 mg)] in a manner similar to that of Example 1-(2) to obtain oily colorless N-(O-benzyl-P-phenethylphosphonyl)-Nle-Trp-OBzl (150 mg).

TLC $Rf^1$ 0.27

LSIMS: m/z=666.3 (M+)

IR $\nu$max(KBr)cm$^{-1}$: 1740 (C=O), 1660 (NHC=O), 1500 (Ar), 1190 (P=O)

NMR $\delta$ppm(CDCl$_3$): 0.80-0.87 (3H, m), 1.16-1.28 (4H, m), 1.41-1.83 ( 2H, m), 1.83-2.01 ( 2H, m), 2.74-2.90 (3H, m), 3.25-3.30 (2H, m), 3.67-3.79 (1H, m), 4.73-5.13 (5H, m), 6.66-7.85 (22H, m)

(3) N-(Phenethylphosphonyl)-Nle-Trp.2Na

N-(O-Benzyl-P-phenethylphosphonyl)-Nle-Trp-OBzl (31.0 mg) obtained in (2) was subjected to catalytic reduction in a manner similar to that of Example 1-(3) to obtain powdery N-(phenethylphosphonyl)-Nle-Trp.2Na (13.3 mg).

TLC $Rf^2$ 0.58

LSIMS: m/z=530.2 [M+H$^+$]

EXAMPLE 7

N-(Phenethylphosphonyl)-Leu-Phe.2Na (1) Boc-Leu-Phe-OBzl

Phe-OBzl.Tos (purchased from Peptide Laboratory) (7.27 g) was condensed with Boc-Leu-ONB [prepared from Boc-Leu-OH.H$_2$O (3.93 g), HONB (3.20 mg) and DCC (3.68 g)] in a manner similar to that of Example 1-(1) to obtain needle crystalline colorless Boc-Leu-Phe-OBzl (5.64 g).

Melting point: 100°-101° C., TLC $Rf^1$ 0.66

$[\alpha]^D_{25}$= -35.3° (C=1.04, MeOH)

Elemental analysis: as C$_{27}$H$_{36}$N$_2$O$_5$ Calculated: C: 69.21; H: 7.74; N: 5.98. Found: C: 69.42; H: 7.70; N: 6.05.

(2) N-(O-Benzyl-P-Phenethylphosphonyl)-Leu-phe-OBzl 1,2-Ethanedithiol (0.2 ml) and 8N hydrochloric acid-dioxane (20 ml) were added to Boc-Leu-Phe-OBzl (1.50 g) obtained in (1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-phenethyl phosphochloridate [prepared from dibenzylphenethyl phosphonate (1.17 g) and phosphorus pentachloride (800 mg)] in a manner similar to that of Example 1-(2) to obtain needle crystalline colorless N-(O-benzyl-P-phenethylphosphonyl)-Leu-Phe-OBzl (351 mg).

Melting point: 93°-95° C. TLC $Rf^1$ 0.37

Elemental analysis: as C$_{37}$H$_{43}$N$_2$O$_5$P Calculated: C: 70.91; H: 6.92; N: 4.47. Found: C: 70.64; H: 7.04; N: 4.30.

IR $\nu$max(KBr)cm$^{-1}$: 1750 (C=O), 1660 (NHC=O), 1500 (Ar), 1190 (P=O)

NMR $\delta$ppm(CDCl$_3$): 0.85-0.90 (6H, m), 1.23-1.37 (1H, m), 1.48-1.56 (1H, m), 1.59-1.69 (1H, m), 1.92-2.06 (1H, m), 2.26-2.95 (3H, m), 3.01-3.13 (2H, m), 3.73-3.81 (1H, m), 4.87-5.16 (5H, m), 6.69-7.37 (21H, m)

(3) N-(Phenethylphosphonyl)-Leu-Phe.2Na

N-(O-Benzyl-P-phenethylphosphonyl)-Leu-Phe-OBzl (70.0 mg) obtained in (2) as subjected to catalytic reduction in a manner similar to that of Example 1-(3) to obtain powdery N-(phenethylphosphonyl)-Leu-Phe.2Na (52.4 mg).

TLC $Rf^2$ 0.58

LSIMS: m/z=491.1 [M+H$^+$]

EXAMPLE 8

N-(Phenethylphosphonyl)-Leu-Leu.2Na (1) Boc-Leu-Leu-OBzl

Leu-OBzl.Tos (purchased from Peptide Laboratory) (6.69 g) was condensed with Boc-Leu-ONB [prepared from Boc-Leu-OH.H$_2$O (3.93 g), HONB (3.20 mg) and DCC (3.68 g)] in a manner similar to that of Example 1-(1) to obtain needle crystalline colorless Boc-Leu-Leu-OBzl (5.67 g).

Melting point: 90°-91° C., TLC $Rf^1$ 0.94

$[\alpha]^D_{25}$= -51.0° (C=1.00, MeOH)

Elemental analysis: as C$_{24}$H$_{38}$N$_2$O$_5$ Calculated: C: 66.33; H: 8.81; N: 6.45. Found: C: 66.29; H: 8.78; N: 6.48.

(2) N-(O-Benzyl-P-Phenethylphosphonyl)-Leu-Leu-OBzl 1,2-Ethanedithiol (0.2 ml) and 8N hydrochloric acid-dioxane (20 ml) were added to Boc-Leu-Leu-OBzl (1.39 g) obtained in (1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-phenethyl phosphochloridate [prepared from dibenzylphenethyl phosphonate (1.17 g) and phosphorus pentachloride (800 mg)] in a manner similar to that of Example 1-(2) to obtain needle crystalline colorless N-(O-benzyl-P-phenethylphosphonyl)-Leu-Leu-OBzl (385 mg).

Melting point: 141°-143° C., TLC $Rf^1$ 0.52

Elemental analysis: as C$_{34}$H$_{45}$N$_2$O$_5$P Calculated: C: 68.90; H: 7.65; N: 4.73. Found: C: 68.64; H: 7.76; N: 4.50.

IR $\nu$max(KBr)cm$^{-1}$: 1750 (C=O), 1660 (NHC=O), 1500 (Ar), 1200 (P=O)

NMR $\delta$ppm(CDCl$_3$): 0.81-0.95 (12H, m), 1.36-1.76 (6H,m), 2.00-2.14 (2H, m), 2.83-3.14 (3H, m), 4.80-4.90 (1H, m), 4.60-4.66 (1H, m), 4.86-5.16 (4H, m), 6.75-7.39 (16H, m)

(3) N-(Phenethylphosphonyl)-Leu-Leu.2Na

N-(O-Benzyl-P-phenethylphosphonyl)-Leu-Leu-OBzl (70.0 mg) obtained in (2) was subjected to catalytic reduction in a manner similar to that of Example 1-(3) to obtain powdery N-(phenethylphosphonyl)-Leu-Leu.2Na (51.0 mg).

TLC Rf² 0.58
LSIMS: m/z=457.1 [M+H⁺]

EXAMPLE 9

N-(Isoamylphosphonyl)-Leu-Trp.2Na (1) N-(O-Benzyl-P-Isoamylphosphonyl)-Leu-Trp-OBzl 1,2-Ethanedithiol (0.2 ml) and 8N hydrochloric acid-dioxane (20 ml) were added to Boc-Leu-Trp-OBzl (1.20 g) obtained in Example 1-(1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-isoamyl phosphochloridate [prepared from dibenzylisoamyl phosphonate (788 mg) and phosphorus pentachloride (544 mg) by the method described in E. D. Thorsett et al., *Proc. Natl. Acad. Sci. USA*, 79, 2176 (1982)] in a manner similar to that of Example 1-(2) to obtain needle crystalline colorless N-(O-benzyl-P-isoamylphosphonyl)-Leu-Trp-OBzl (253 mg).

Melting point: 78°–80° C., TLC Rf¹ 0.30
Elemental analysis: as $C_{36}H_{46}N_3O_5P$ Calculated: C: 68.44; H: 7.34; N: 6.65. Found: C: 68.23; H: 7.10; N: 6.61.
IR νmax(KBr)cm⁻¹: 1730 (C=O), 1660 (NHC=O), 1530 (Ar), 1200 (P=O)
NMR δppm(CDCl₃): 0.80–0.87 (12H, m), 1.31–1.70 (8H,m), 2.73–2.86 (1H, m), 3.23–3.35 (2H, m), 3.71–3.82 (1H, m), 4.65–5.11 (5H, m), 6.76–8.13 (17H, m)

(2) N-(Isoamylphosphonyl)-Leu-Trp.2Na

N-(O-Benzyl-P-isoamylphosphonyl)-Leu-Trp-OBzl (70.0 mg) obtained in (1) was subjected to catalytic reduction in a manner similar to that of Example 1-(3) to obtain powdery N-(isoamylphosphonyl)-Leu-Trp.2Na (54.0 mg).

TLC Rf² 0.58
LSIMS: m/z=496.1 [M+H⁺]

EXAMPLE 10

N-(Cyclohexylmethylphosphonyl)-Leu-Trp.2Na (1) N-(O-Benzyl-P-Cyclohexylmethylphosphonyl)-Leu-Trp-OBzl 1,2-Ethanedithiol (0.2 ml) and 8N hydrochloric acid-dioxane (20 ml) were added to Boc-Leu-Trp-OBzl (1.20 g) obtained in Example 1-(1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-cyclohexylmethyl phosphochloridate [prepared from dibenzylcyclohexylmethyl phosphonate (1.10 g) and phosphorus pentachloride (767 mg) by the method described in E. D. Thorsett et al., *Proc. Natl. Acad. Sci. USA*, 79, 2176 (1982)] in a manner similar to that of Example 1-(2) to obtain needle crystalline colorless N-(O-benzyl-P-cyclohexylmethylphosphonyl)-Leu-Trp-OBzl (360 mg).

Melting point: 99°–101° C., TLC Rf¹ 0.32
Elemental analysis: as $C_{38}H_{48}N_3O_5P$ Calculated: C: 69.39; H: 7.36; N: 6.39. Found: C: 69.13; H: 7.42; N: 6.31.
IR νmax(KBr)cm⁻¹: 1740 (C=O), 1660 (NHC=O), 1560 (Ar), 1200 (P=O)
NMR δppm(CDCl₃): 0.81–0.88 (6H, m), 0.88–1.99 (16H,m), 2.92–3.05 (1H, m), 3.22–3.35 (2H, m), 3.70–3.80 (1H, m), 4.66–5.10 (5H, m), 6.35–8.31 (17H, m)

(2) N-(Cyclohexylmetylphosphonyl)-Leu-Trp.2Na

N-(O-Benzyl-P-cyclohexylmethylphosphonyl)-Leu-TrP-OBzl (70.0 mg) obtained in (1) was subjected to catalytic reduction in a manner similar to that of Example 1-(3) to obtain powdery N-(cyclohexylmethylphosphonyl)-Leu-TrP.2Na (48.1 mg).

TLC Rf² 0.58
LSIMS: m/z=522.2 [M+H⁺]

EXAMPLE 11

N-(1-Naphthylmethylphosphonyl)-Leu-TrP.2Na (1) N-[O-Benzyl-P-(1-Naphthyl)methylphosphonyl]-Leu-TrP-OBzl 1,2-Ethanedithiol (0.2 ml) and 8N hydrochloric acid-dioxane (20 ml) were added to Boc-Leu-Trp-OBzl (1.64 g) obtained in Example 1-(1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-(1-naphthyl)methyl phosphochloridate [prepared from dibenzyl 1-naphthylmethyl phosphonate (1.30 g) and phosphorus pentachloride (792 mg) by the method described in E. D. Thorsett et al., *Proc. Natl. Acad. Sci. USA*, 79, 2176 (1982)] in a manner similar to that of Example 1-(2) to obtain needle crystalline colorless N-[O-benzyl-P-1-naphthyl)methylphosphonyl]-Leu-Trp-OBzl (560 mg).

Melting point: 54.0°–56.0° C., TLC Rf¹ 0.42
Elemental analysis: as $C_{42}H_{44}N_3O_5P$ Calculated: C: 71.88; H: 6.32; N: 5.99. Found: C: 71.77; H: 6.45; N: 5.95.
IR νmax(KBr)cm⁻¹: 1740 (C=O), 1660 (NHC=O), 1510 (Ar), 1210 (P=O)
NMR δppm(CDCl₃): 0.60–0.81 (6H, m), 0.92–1.00 (1H, m), 1.20–1.57 (2H, m), 2.65–2.80 (1H, m), 3.20–3.81 (5H, m), 4.61–5.10 (5H, m), 6.57–8.05 (24H, m)

(2) N-(1-Naphthylmethylphosphonyl)-Leu-Trp.2Na

N-[O-Benzyl-P-(1-naphthyl)methylphosphonyl]-Leu-Trp-OBzl (30.0 mg) obtained in (1) was subjected to catalytic reduction in a manner similar to that of Example 1-(3) to obtain powdery N-(1-naphthylmethylphosphonyl)-Leu-Trp.2Na (17.5 mg).

TLC Rf² 0.62
LSIMS: m/z=566.1 [M+H⁺]

EXAMPLE 12

N-(2-Naphthylmethylphosphonyl)-Leu-Trp.2Na (1) N-[O-Benzyl-P-(2-Naphthyl)methylphosphonyl]-Leu-Trp-OBzl 1,2-Ethanedithiol (0.2 ml) and 8N hydrochloric acid-dioxane (20 ml) were added to Boc-Leu-Trp-OBzl (1.64 g) obtained in Example 1-(1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-(2-naphthyl)methyl phosphochloridate [prepared from dibenzyl 2-naphthylmethyl phosphonate (1.30 g) and phosphorus pentachloride (792 mg) by the method described in E. D. Thorsett et al., *Proc. Natl. Acad. Sci. USA*, 79, 2176 (1982)] in a manner similar to that of Example 1-(2) to obtain needle crystalline colorless N-[O-benzyl-P-(2-naphthyl)methylphosphonyl]-Leu-Trp-OBzl (160 mg).

Melting point: 59.0°–61.0° C., TLC Rf¹ 0.45

Elemental analysis: as C₄₂H₄₄N₃O₅P Calculated: C: 71.88; H: 6.32; N: 5.99. Found: C: 71.59; H: 6.38; N: 5.97.

IR νmax(KBr)cm⁻¹: 1740 (C=O), 1660 (NHC=O), 1460 (Ar), 1220 (P=O)

NMR δppm(CDCl₃): 0.63–0.81 (6H, m), 1.10–1.29 (1H, m), 1.40–1.50 (1H, m), 1.50–1.63 (1H, m), 2.64–2.76 (1H, m), 3.02–3.30 (4H, m), 3.69–3.80 (1H, m), 4.65–5.10 (5H, m), 6.48–7.97 (24H, m)

(2) N-(2-Naphthylmethylphosphonyl)-Leu-Trp.2Na

N-[O-Benzyl-P-(2-naphthyl)methylphosphonyl]-Leu-Trp-OBzl (50.0 mg) obtained in (1) was subjected to catalytic reduction in a manner similar to that of Example 1-(3) to obtain powdery N-(2-naphthylmethylphosphonyl)-Leu-Trp.2Na (24.5 mg).

TLC Rf² 0.65

LSIMS: m/z=566.1 [M+H⁺]

EXAMPLE 13

N-[2-(1-Naphthyl)ethylphosphonyl]-Leu-Trp.2Na (1) N-[O-Benzyl-P-[2-(1-Naphthyl)]ethylphosphonyl]-Leu-Trp-OBzl 1,2-Ethanedithiol (0.2 ml) and 8N hydrochloric acid-dioxane (20 ml) were added to Boc-Leu-Trp-OBzl (2.17 g) obtained in Example 1-(1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-[2-(1-naphthyl)]ethyl phosphochloridate [prepared from dibenzyl 2-(1-naphthyl)ethyl phosphonate (1.65 g) and phosphorus pentachloride (1.07 g) by the method described in E. D. Thorsett et al., Proc. Natl. Acad. Sci. USA, 79, 2176 (1982)] in a manner similar to that of Example 1-(2) to obtain needle crystalline colorless N-[O-benzyl-P-[2-(1-naphthyl)]ethylphosphonyl]-Leu-Trp-OBzl (420 mg).

Melting point: 51.5°–54.0° C., TLC Rf¹ 0.28

Elemental analysis: as C₄₃H₄₆N₃O₅P Calculated: C: 72.15; H: 6.48; N: 5.87. Found: C: 72.08; H: 6.40; N: 5.74.

IR νmax(KBr)cm⁻¹: 1740 (C=O), 1660 (NHC=O), 1460 (Ar), 1200 (P=O)

NMR δppm(CDCl₃): 0.75–0.90 (6H, m), 1.23–1.39 (1H, m), 1.46–1.71 (2H, m), 1.83–2.00 (1H, m), 2.00–2.13 (1H, m), 2.75–2.83 (1H, m), 3.13–3.38 (4H, m), 3.75–3.87 (1H, m), 4.73–5.60 (5H, m), 6.66–7.97 (24H, m)

(2) N-[2-(1-Naphthyl)ethylphosphonyl]-Leu-Trp.2Na

N-[O-Benzyl-P-[2-(1-naphthyl)ethylphosphonyl]-Leu-Trp-OBzl (50.0 mg) obtained in (1) was subjected to catalytic reduction in a manner similar to that of Example 1-(3) to obtain powdery N-[2-(1-naphthyl)ethylphosphonyl]-Leu-Trp.2Na (31.2 mg).

TLC Rf² 0.63

LSIMS: m/z=580.1 [M+H⁺]

EXAMPLE 14

N-[2-(2-Naphthyl)ethylphosphonyl]-Leu-Trp.2Na (1) N-[O-Benzyl-P-[2-(2-Naphthyl)]ethylphosphonyl]-Leu-Trp-OBzl 1,2-Ethanedithiol (0.2 ml) and 8N hydrochloric acid-dioxane (20 ml) were added to Boc-Leu-Trp-OBzl (2.17 g) obtained in Example 1-(1) under ice cooling to dissolve it, followed by stirring for 30 minutes. The solvent was removed by distillation under reduced pressure, and diethyl ether was added to the residue to precipitate crystals. The crystals were filtered off and dried. The resulting product was reacted with O-benzyl-P-[2-(2-naphthyl)]ethyl phosphochloridate [prepared from dibenzyl 2-(2-naphthyl)ethyl phosphonate (1.65 g) and phosphorus pentachloride (1.07 g) by the method described in E. D. Thorsett et al., Proc. Natl. Acad. Sci. USA, 79, 2176 (1982)] in a manner similar to that of Example 1-(2) to obtain needle crystalline colorless N-[O-benzyl-P-[2-(2-naphthyl)]ethylphosphonyl]-Leu-Trp-OBzl (850 mg).

Melting point: 51.5°–53.0° C., TLC Rf¹ 0.40

Elemental analysis: as C₄₃H₄₆N₃O₅P Calculated: C: 72.15; H: 6.48; N: 5.87. Found: C: 72.05; H: 6.42; N: 5.79.

IR νmax(KBr)cm⁻¹: 1740 (C=O), 1660 (NHC=O), 1510 (Ar), 1200 (P=O)

NMR δppm(CDCl₃): 0.80–0.88 (6H, m), 1.25–1.37 (1H, m), 1.50–1.56 (1H, m), 1.56–1.70 (1H, m), 1.91–2.00 (1H, m), 2.00–2.10 (1H, m), 2.68–2.81 (1H, m), 2.89–3.06 (2H, m), 3.26–3.30 (2H, m), 3.73–3.84 (1H, m), 4.72–5.10 (5H, m), 6.65–7.84 (24H, m)

(2) N-[2-(2-Naphthyl)ethylphosphonyl]-Leu-Trp.2Na

N-[O-Benzyl-P-[2-(2-naphthyl)ethylphosphonyl]-Leu-Trp-OBzl (50.0 mg) obtained in (1) was subjected to catalytic reduction in a manner similar to that of Example 1-(3) to obtain powdery N-[2-(2-naphthyl)ethylphosphonyl]-Leu-Trp.2Na (26.1 mg).

TLC Rf² 0.66

LSIMS: m/z=580.1 [M+H⁺]

What is claimed is:

1. A compound represented by formula [I] or a pharmaceutically acceptable salt thereof:

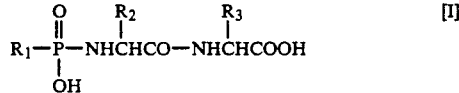

wherein

R₁ is (i) a C₁₋₁₂ alkyl group which may substituted by C₃₋₈ cycloalkyl, halogen, hydroxy which may be protected, C₁₋₂ alkoxy, ketone or amino which may be protected, (ii) a 5 to 7 member cycloalkyl group which may be substituted by lower alkyl having 1 to 3 carbon atoms, halogen, hydroxy which may be protected, C₁₋₂ alkoxy, keto, or amino which may be protected or (iii) an aralkyl group which may be substituted by lower alkyl having 1 to 3 carbon atoms, C₅₋₆ cycloalkyl, halogen, hydroxy which may be protected, or C₁₋₂ alkoxy;

R₂ is (i) a C₁₋₈ alkyl group (ii) a cyclohexylmethylene group or (iii) a benzyl group; and R₃ is an indolylmethyl group or a benzyl group.

2. The compound according to claim 1, in which R₁ is selected from the group which consists of an alkyl group having 1 to 12 carbon atoms; a 5-, 6- or 7-membered alicyclic alkyl group; and an alkyl group having 1 to 5 carbon atoms substituted by an aromatic hydrocarbon group having 6 to 12 carbon atoms.

3. The compound according to claim 2, in which said alkyl group having 1 to 12 carbon atoms is isoamyl or cyclohexylmethyl, and said alkyl group having 1 to 5 carbon atoms substituted by the aromatic hydrocarbon group is phenylethyl, naphthylmethyl or naphthylethyl.

4. The compound according to claim 1, in which said indolylmethyl group is indol-3-ylmethyl.

5. A compound represented by formula [I] or a pharmaceutically acceptable salt thereof:

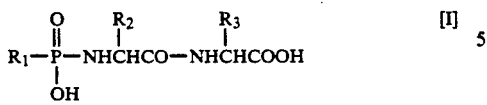

wherein $R_1$ is isoamyl, cyclohexylmethyl, phenethyl, naphthylmethyl or naphthylethyl, $R_2$ is isobutyl or benzyl, and $R_3$ is indol-3-ylmethyl.

6. The compound according to claim 5, in which said compound is N-(phenethylphosphonyl)-leucyl-tryptophan.

7. The compound according to claim 5, in which said compound is N-(cyclohexylmethylphosphonyl)-leucyl-tryptophan.

8. The compound according to claim 5, in which said compound is N-(1-naphthylmethylphosphonyl)-leucyl-tryptophan.

9. The compound according to claim 5, in which said compound is N-{2-(1-naphthyl)ethylphosphonyl}-leucyl-tryptophan.

10. The compound according to claim 5, in which said compound is N-{2-(2-naphthyl)ethylphosphonyl}-leucyl-tryptophan.

11. A pharmaceutical composition comprising the compound or the pharmaceutically acceptable salt thereof claimed in claim 5 and a pharmaceutically acceptable carrier.

12. A method for bringing about endothelin-converting enzyme inhibiting activity in a warm-blood animal, which comprises administering an effective amount of the compound or the pharmaceutically acceptable salt thereof claimed in claim 5 to the warm-blood animal.

13. A compound represented by formula [I] or a pharmaceutically acceptable salt thereof:

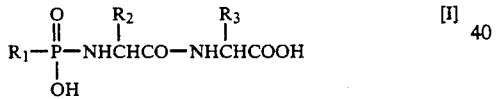

wherein
$R_1$ is (i) a $C_{1-12}$ alkyl group which may substituted by $C_{3-8}$ cycloalkyl, halogen, hydroxy which may be protected, $C_{1-2}$ alkoxy, or amino which may be protected, (ii) a 5 to 7 member cycloalkyl group which may be substituted by lower alkyl having 1 to 3 carbon atoms, halogen, hydroxy which may be protected, $C_{1-2}$ alkoxy, keto, or amino which may be protected, or (iii) a $C_{7-17}$ aralkyl group which may be substituted by lower alkyl having 1 to 3 carbon atoms, $C_{5-6}$ cycloalkyl, halogen, hydroxy which may be protected, or $C_{1-2}$ alkoxy;

$R_2$ is (i) a $C_{1-8}$ alkyl group, (ii) a 5 to 7 member cycloalkyl group, or (iii) a benzyl group; and $R_3$ is a $C_{1-8}$ alkyl group which is substituted by 3-indolyl.

14. A compound represented by formula [I] or a pharmaceutically acceptable salt thereof:

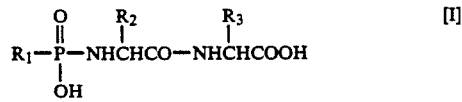

wherein $R_1$ is phenethyl, isoamyl, cyclohexylmethyl, naphthylmethyl or naphthylethyl, R2 is propyl, butyl, cyclohexylmethyl or benzyl and $R_3$ is benzyl or indolylmethyl.

15. A compound represented by formula [I] or a pharmaceutically acceptable salt thereof:

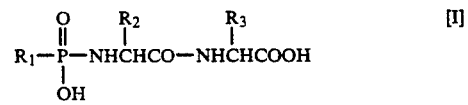

wherein
$R_1$ is an alkyl group of 1 to 12 carbon atoms or an alkyl group having 1 to 5 carbon atoms substituted by an aromatic hydrocarbon group having 6 to 12 carbon atoms;

$R_2$ is an alkyl group having 1 to 8 carbon atoms; an alkyl group having 1 to 8 carbon atoms substituted by a cycloalkyl group having 5 to 7 carbon atoms; or an alkyl group having 1 to 5 carbon atoms substituted by an aromatic hydrocarbon group having 6 to 12 carbon atoms; and $R_3$ is alkyl having 1 to 8 carbon atoms substituted by indolyl or an aromatic hydrocarbon group having to 6 to 12 carbon atoms.

16. The compound of claim 15 wherein $R_1$ is isoamyl, cyclohexylmethyl, phenylethyl, napthylmethyl or naphthylethyl; $R_2$ is isobutyl or benzyl, and $R_3$ is indolylmethyl or benzyl.

* * * * *

UNITED STATES PATENT AND TRADEMARK OFFICE
CERTIFICATE OF CORRECTION

PATENT NO. : 5,330,978

DATED : July 19, 1994

INVENTOR(S) : Wakimasu, et al.

It is certified that error appears in the above-identified patent and that said Letters Patent is hereby corrected as shown below:

Column 20, line 42, insert --be-- after "may".

Column 21, line 45, insert --be-- after "may".

Signed and Sealed this

Twentieth Day of December, 1994

Attest:

BRUCE LEHMAN

*Attesting Officer*    *Commissioner of Patents and Trademarks*

REEXAMINATION CERTIFICATE (2925th)
United States Patent [19]
Wakimasu et al.

[11] B1 5,330,978
[45] Certificate Issued Jun. 18, 1996

[54] PHOSPHONIC ACID DERIVATIVES AND USE THEREOF

[75] Inventors: Mitsuhiro Wakimasu; Masaaki Mori; Akira Kawada, all of Ibaraki, Japan

[73] Assignee: Takeda Chemical Industries, Ltd., Osaka, Japan

Reexamination Request:
No. 90/004,000, Oct. 18, 1995

Reexamination Certificate for:
Patent No.: 5,330,978
Issued: Jul. 19, 1994
Appl. No.: 892,768
Filed: Jun. 3, 1992

Certificate of Correction issued Dec. 20, 1994.

[30] Foreign Application Priority Data

Jun. 13, 1991 [JP] Japan ................................... 3-142099
Apr. 9, 1992 [JP] Japan ................................... 4-089111

[51] Int. Cl.⁶ .............................. C07F 9/22; A61K 33/42
[52] U.S. Cl. ..................... 514/80; 514/118; 548/414; 558/171
[58] Field of Search ................ 514/80, 118; 548/414; 558/171

[56] References Cited

U.S. PATENT DOCUMENTS

4,379,146  4/1983  Greenlee et al. ............... 424/177
4,432,972  2/1994  Karanewsky et al. ............ 424/177

OTHER PUBLICATIONS

Merz et al, "Free Energy Perturbation Simulations of the Inhibition of Thermolysin: Prediction of the Free Energy of Binding of a New Inhibitor", *J. Am. Chem. Soc.*, vol. 111, No. 15 (1989), pp. 5649–5658.

Mookhtiar, K. A. et al "Phosphonamidate Inhibitors of Human Neutrophil Collagenase". *Biochemistry*, vol. 26, No. 7 (1987) (pp. 1962–1965).

McMahon et al, "Phosphoramidon Blocks The Pressor Activity of Porcine Big Endothelin-1-(1–39) In Vivo and Conversion of Big Endothelin-1-(1–39), 2 Endothelin-1-(1–21) In Vitro", *Proceedings National Academy of Science*, vol. 88 (Feb. 1991), pp. 703–707.

Fukuroda, T. et al, "Inhibition of Biological Action of Big Endothelin-1 by Phosphoramidon", *Biochemical and Biophysical Research Communication*, vol. 172, No. 2 (Oct. 30, 1990), pp. 390–395.

Rich, H. David, "Peptidase Inhibitors" in *Comprehensive Medicinal Chemistry The Rational Design, Mechanistic Study & Therapeutic Application of Chemical Compounds*, vol. 2 (Pergamon Press PLC), pp. 391–496 (not continuous), 1990.

Kam, C. M. et al, "Inhibition of Thermolysin and Carboxy Peptidase A Biphosphoramides". *Biochemistry*, vol. 18, No. 14 (1979), pp. 3032–3038.

Wakimasu, Rule 132 Declaration, Paper #10, File Wrapper of U.S. Patent No. 5,330,978 (Admissions).

Carey et al, "Reactions and Synthesis": Chapter 11 entitled Multistep Synthesis at pp. 539–553, *Advanced Organic Chemistry*, Second Ed. Part B (New York Plenum Press, 1983).

*Primary Examiner*—David B. Springer

[57] ABSTRACT

A phosphonic acid derivative compound represented by formula [I] or a pharmaceutically acceptable salt thereof:

wherein $R_1$, $R_2$ and $R_3$ each represent hydrocarbon groups which may be substituted, except cases in which (1) $R_2$ is unsubstituted methyl, (2) $R_3$ is an unsubstituted hydrocarbon group having 1 to 3 carbon atoms, and (3) $R_1$ is benzyloxycarbonylaminomethyl, $R_2$ is isobutyl and $R_3$ is isobutyl or phenylmethyl, which has endothelin-converting enzyme inhibiting activity and is useful as pharmaceutical drugs such as therapeutic agents for hypertension, cardiac or cerebral circulatory diseases and renal diseases.

B1 5,330,978

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–16 is confirmed.

* * * * *